United States Patent
Hoffmann et al.

[11] Patent Number: 6,103,264
[45] Date of Patent: Aug. 15, 2000

[54] PROCESS FOR PREPARING A CONTROLLED RELEASE COMPOSITION

[75] Inventors: Torsten Hoffmann; Klaus Liebold, both of Dresden; Joachim Wolf, Radebeul; Heiko Schumacher, Aschaffenberg, all of Germany

[73] Assignee: Arzneimittelwerk Dresden GmbH, Germany

[21] Appl. No.: 09/110,709

[22] Filed: Jul. 7, 1998

[30] Foreign Application Priority Data

Jul. 10, 1997 [DE] Germany ............... 197 29 487

[51] Int. Cl.[7] .............. A61K 9/28; A61K 9/48; A61K 9/22; A61K 9/52

[52] U.S. Cl. ............ 424/468; 424/451; 424/452; 424/465; 424/474; 424/475; 424/484; 424/486; 424/487; 424/469; 424/470; 424/464; 424/457; 514/772.3; 514/784; 514/785; 514/786; 514/787

[58] Field of Search ............... 424/451, 452, 424/468, 470, 469, 463–465, 474, 457, 479, 480, 482, 475, 484, 486, 487

[56] References Cited

FOREIGN PATENT DOCUMENTS

| 654263 | of 0000 | European Pat. Off. . |
|---|---|---|
| 351580 | 1/1990 | European Pat. Off. . |
| 672416 | 9/1995 | European Pat. Off. . |
| 729751 | 9/1996 | European Pat. Off. . |
| 1617593 | of 0000 | Germany . |
| 93/07859 | of 0000 | WIPO . |
| 93/18753 | 9/1993 | WIPO . |

*Primary Examiner*—James M. Spear
*Attorney, Agent, or Firm*—Schweitzer Cornman Gross & Bondell LLP

[57] ABSTRACT

A process for preparing a controlled release composition with a controlled release matrix and containing a pharmaceutically active ingredient, which comprises granulating the active ingredient with a molten matrix material or with a matrix material while it is being melted and with optional additional inactive materials at a first elevated temperature, then cooling and screening the granulate, forming a fluidized bed of the resulting material at a second elevated temperature, and recovering the resulting product; and the product formed by the process.

17 Claims, 3 Drawing Sheets

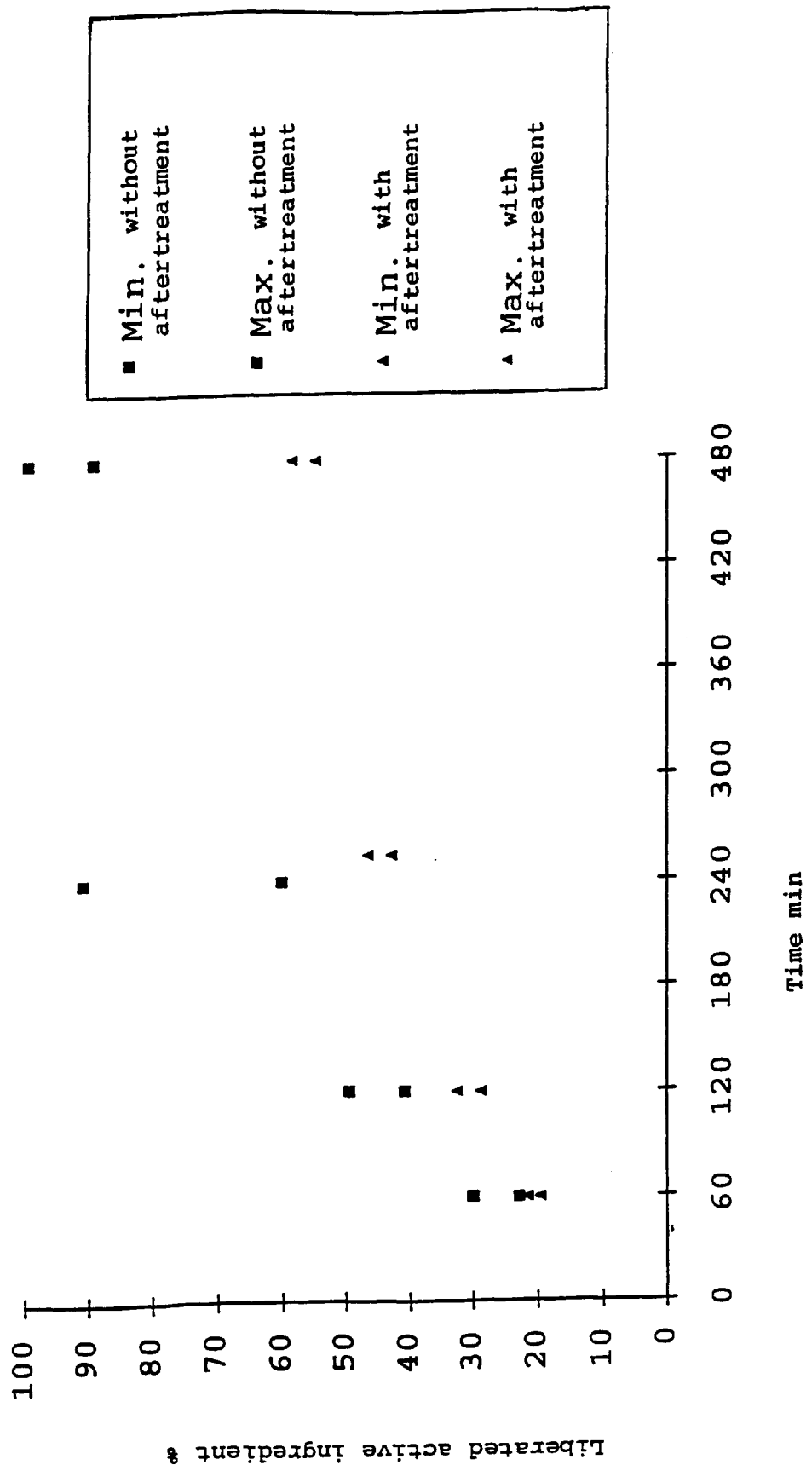

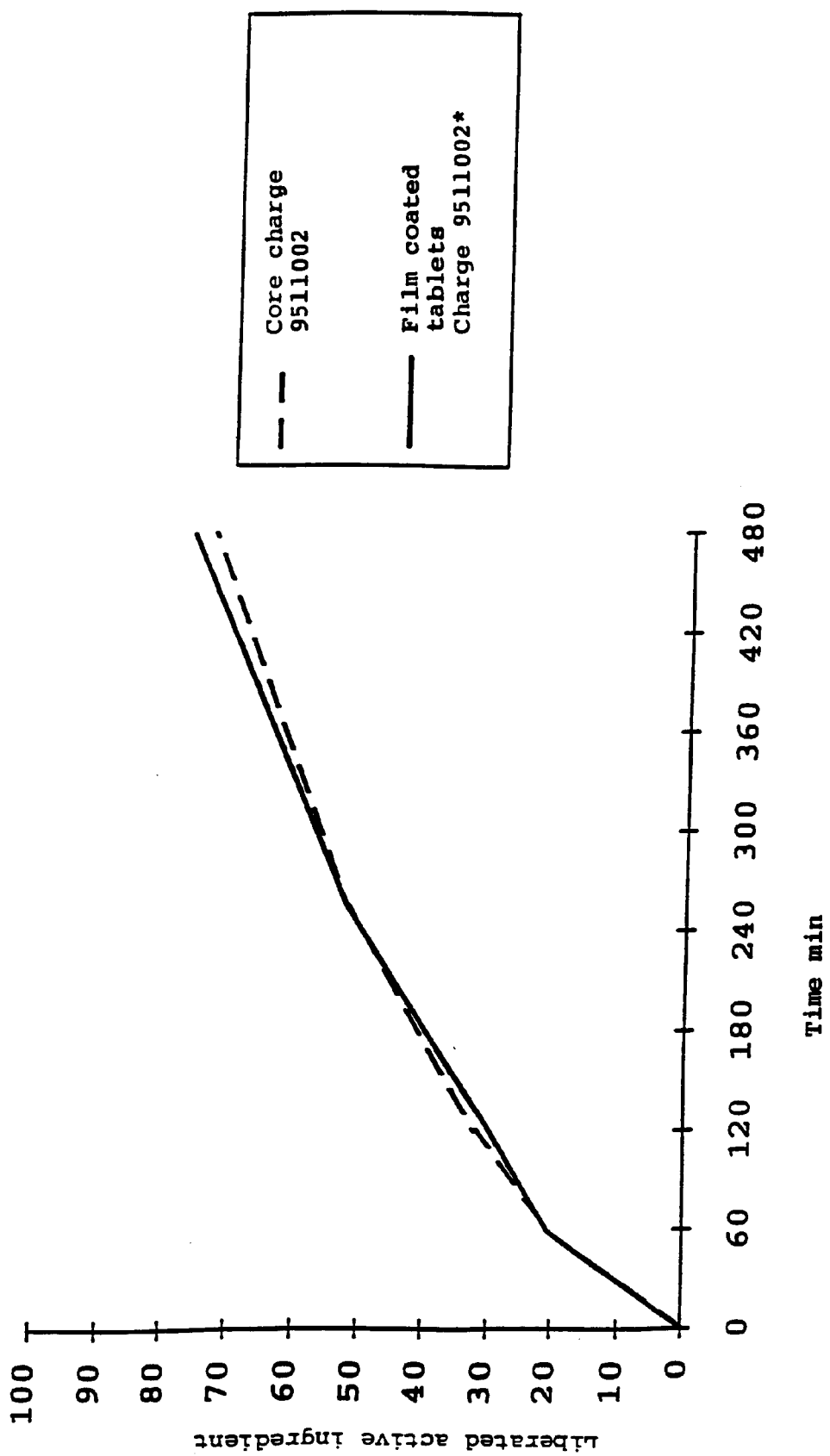

PROCESS FOR PREPARING A CONTROLLED RELEASE COMPOSITION

FIELD OF INVENTION

The present invention relates to a novel method for preparing compositions with a controlled release of an active ingredient from a matrix.

BACKGROUND

Controlled release dosage drug forms represent a form of drug administration, which has been largely adapted to the therapeutic requirements and the drug, the release of which is controlled by mechanisms which are not affected or affected to only an insignificant extent by physiological conditions such as pH, enzymes, nature and quality of the food. Depending on the control principles employed, diffusion-, matrix-, swelling-membrane-, or chemically-controlled release can occur. According to the more comprehensive definition of the American Food and Drug Administration, controlled-release products are formulations intended to release the active component at rates which differ significantly from the immediate release from corresponding compositions not having any delaying properties. This definition includes all types of retard (sustained-release) drug forms, as well as those with fixed time release properties, such as preparations resistant to gastric juices.

A number of methods for preparing such formulations are known from the literature. For example, the European patent No. 324,989 discloses the preparation of a new pharmaceutical formulation with controlled release by means of wet granulation, the active ingredient being mixed with appropriate inactive ingredients and granulated in 95% ethanol. After subsequent drying, the granulate obtained is screened to the desired size.

Formulations with a controlled release can also be prepared by melt granulation, as described, for example, in the German patent No.2,426,812. The binder component is present here in a liquid aggregate state, since the process temperature for the granulation is higher than the melting temperature of the low-melting component.

Further methods of producing formulations with controlled release, known from the art, are various granulation and extrusion methods as described, for example, in German patent No. 4,408,326.

The active compositions, obtained with the known methods, in some cases have an incomplete release delay or much scatter in the individual values for the release of active ingredient. This can have a particularly disadvantageous effect for patients, since it cannot be assured that the desired plasma concentration and the corresponding level of bio-availability can be maintained.

SUMMARY OF THE INVENTION

It is an object of the present invention to develop a new, technically simple method for the preparation of controlled release formulations, which enables the reproducible release of the active ingredient.

This objective is accomplished pursuant to the present invention by the active ingredient with a molten matrix material or with a matrix material while it is being melted and with optional additional inactive materials at a first elevated temperature, then cooling and screening the granulate, forming a fluidized bed of the resulting material at a second elevated temperature, and recovering the resulting product.

In the process the active ingredient, which can be water-soluble or water-insoluble, is added to an intensive mixer or is previously mixed with the inactive ingredients and, with the addition of binders or binder mixtures, which either are melted during the addition or are being melted only during the process in the intensive mixer, is granulated at temperatures between about 10° C. and about 100° C. in the intensive mixer.

High speed mixers with or without heating and cooling jackets, such as the Gral, Collette, or Diosna, can be used as the intensive mixer. The method of the present invention is particularly advantageous when used with mixers which do not have a heating jacket.

After cooling the obtained granulate, it can be screened through, for example, a sieve of 3.0 mm mesh size and heated in a fluidized bed of a fluidized bed granulator until the melting point of the binder used in the mixture is reached. The treatment is continued suitably in the temperature range of from about 30° C. to about 100° C. with addition of heated air until the fluidized bed almost collapses, and then the product is cooled once again.

After this subsequent thermal treatment the granulate is screened once more and is then mixed with suitable tabletting aids, and pressed into tablets and optionally coated with a film or with sugar, or can be filled into capsules. Coatings can be based, for example, on polymethacrylic acid derivatives or cellulose derivatives.

The preparation of formulations with controlled release according to the method of the present invention is particularly suitable for non-steroidal anti-inflammatories, broncholytics, vasodilators, muscle relaxants, anti-rheumatics such as diclofenac, antiphlogistics, antiepileptics such as carbamazepine, antihypertensives, antihistamines, anticoagulants, intestinal drugs, cytostatics, calcium channel blockers such as verapamil, and cardiac drugs.

Substances having a melting point between about 35° C. and about 95° C. can be used as binders. Suitable binder materials include water-soluble or swellable binders, such as macrogol, polyvidone, polymethacrylic acid derivatives (Eudragit), lipophilic binders, such as paraffin, cetyl palmitate, fatty alcohols such as cetyl alcohol, beeswax, carnauba wax, hydrogenated vegetable oils, triglycerides, and stearic acid. These exemplary substances represent only a partial listing of suitable materials. Thus, formulations can be prepared with controlled release properties also with other active substances and binders generally well known per se.

It could not have been expected that the formulations prepared from granulates by the method of the present invention provide reproducible, controlled release rates with very little scattering between individual values even when the formulations are changed. Surprisingly, the specific release characteristics can be adjusted by the subsequent thermal aftertreatment in accordance with the present invention.

The aftertreatment of the invention is carried out by heating in the fluidized bed after a prior surface enlargement by screening, the active ingredient is embedded or enveloped completely by the binder in the matrix depending on the formulation. This leads to a retarded release that conforms to the specifications without deviations in the active ingredient content that could have been expected to result from any disproportionate losses in the fluidized bed.

BRIEF DESCRIPTION OF THE DRAWINGS

The present invention is further disclosed with reference being had to the attached drawing, wherein

FIG. 2 shows the scatter of the individual values of the release rate of the active ingredient from the two dosage forms shown in FIG. 1; and FIG. 3 shows the release rate determined exclusively by the core and consequently by the granulation conditions since the coating does not have a significant effect on the release rate of active ingredient.

DETAILED DESCRIPTION

Figure 1:
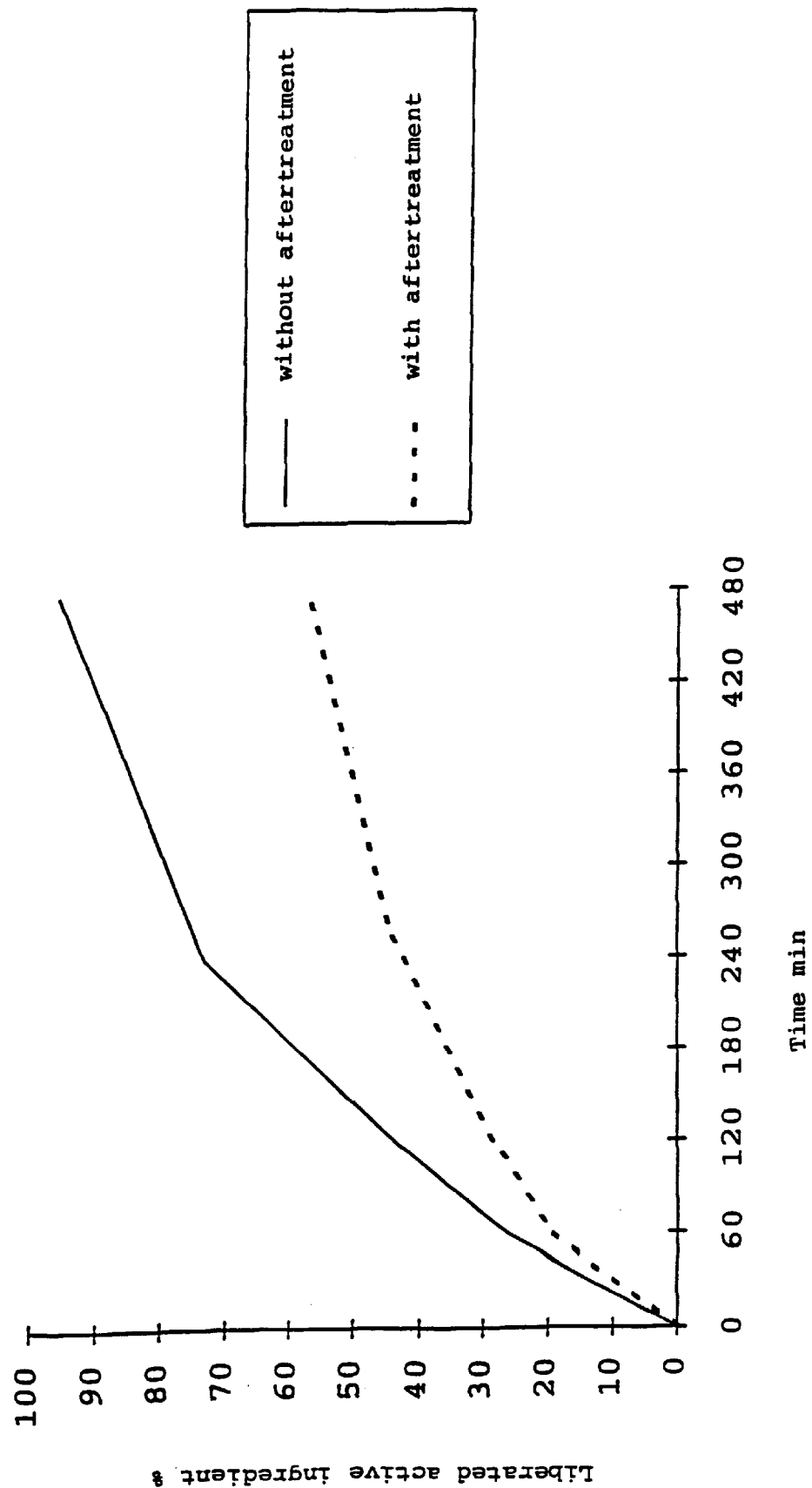
FIG. 1 shows the effect of the aftertreatment in accordance with the present invention on the release rate of the active ingredient, diclofenac sodium, and compares this release rate with that of a granulate produced by conventional melt granulation in the known intensive mixer in a known manner without the aftertreatment of the invention.

The method of the present invention can be used generally for achieving specific release rates since such specific availabilities of the active can be attained by the ensured optimum embedding or enveloping of the drug or drugs and by the choice of a suitable binder.

The following examples further explain the method of the present invention.

EXAMPLE 1

A tablet containing 100 mg of diclofenac sodium in a 263.3 mg tablet of:

| | |
|---|---|
| sucrose | 105.00 mg |
| diclofenac sodium | 100.00 mg |
| cetyl alcohol | 55.20 mg |
| silica | 0.52 mg |
| magnesium stearate | 1.30 mg |
| polyvidone | 1.28 mg |
| Total | 263.30 mg |

The sucrose and the active ingredient, diclofenac sodium, are mixed, then the molten cetyl alcohol (at about 65° C.±2° C.) is added in an intensive mixer. After a granulation time of less than 10 minutes, there is an increase in power consumption and the granulation is terminated. The granulate is screened and it is treated in a fluidized bed granulator, with the incoming air having a temperature of from about 60° C. to about 75° C. The binder begins to melt at about 43° C. product temperature, and further formation of granulate sets in. The end point of the granulation is reached before the fluidized bed collapses, and the product is then cooled.

The product is next screened again. After the addition of silica, magnesium stearate and polyvidone, mixing is carried out and the resulting tabletting mixture is pressed into tablets containing 100 mg of active ingredient.

EXAMPLE 2

A tablet, containing 120 mg of verapamil hydrochloride in a 410 mg

| | |
|---|---|
| verapamil hydrochloride | 120 mg |
| cetyl alcohol | 183 mg |
| cellulose | 101 mg |

-continued

| | |
|---|---|
| silica | 2 mg |
| magnesium stearate | 4 mg |
| Total | 410 mg |

The active ingredient, verapamil hydrochloride, is added to the molten cetyl alcohol while stirring in an intensive mixer. After a short granulating time the granulate is removed, screened and then heated in a fluidized bed. The desired melting commences at a product temperature of about 43° C. and continues up to an end point, before the fluidized bed collapses. After that, the product is cooled immediately, screened and mixed with silica and magnesium stearate. Tablets, containing 120 mg of verapamil hydrochloride, are produced.

EXAMPLE 3

A 410 mg tablet:

| | |
|---|---|
| verapamil hydrochloride | 120 mg |
| cetyl alcohol | 66 mg |
| cellulose | 101 mg |
| sucrose | 117 mg |
| silica | 2 mg |
| magnesium stearate | 4 mg |
| Total | 410 mg |

The procedure is similar to that of Examples 1 and 2.

We claim:

1. A process for preparing a controlled release composition with a controlled release matrix and containing a pharmaceutically active ingredient, which comprises granulating said active ingredient with a molten matrix material or with a matrix material while it is being melted and with optional additional inactive materials at a first elevated temperature, then cooling and screening the granulate, forming a fluidized bed of the resulting material at a second elevated temperature, and recovering the resulting product.

2. The process of claim 1, wherein said recovering comprises cooling the resulting product.

3. The process of claim 2, wherein said step of recovering further comprises screening the cooled resulting product.

4. The process of claim 3, further comprising finishing the screened resulting product by filling it into capsules, or compressing it into tablets.

5. The process of claim 4, further comprising sugar coating or film coating said tablets.

6. The product of the process of claim 1.

7. The process of claim 1, wherein said pharmaceutically active ingredient is a nonsteroidal antiinflammatory, broncholytic, vasodilator, muscle relaxant, antirheumatic, antiphlogistic, antiepileptic, antihistamine, anticoagulant, intestinal drug, cytostatic, calcium antagonist, or cardiac drug.

8. The process of claim 7, wherein said antirheumatic is diclofenac, said antiepileptic is carbamazepine, and said calcium antagonist is verapamil.

9. The process of claim 1, wherein said matrix material has a melting point of from about 35° C. to about 95° C.

10. The process of claim 9, wherein said matrix material is a water soluble or water swellable material, or a lipophylic binder.

11. The process of claim 10, wherein said material is one or more of macrogol, polyvidone, a polymethacrylic acid derivative, or one or more lipophylic binder.

12. The process of claim 11, wherein said lipophylic binder is one or more of paraffin, cetyl palmitate, a fatty alcohol, beeswax, carnauba wax, hydrogenated vegetable oil, triglyceride, and stearic acid.

13. The process of claim 12, wherein said fatty alcohol is cetyl alcohol.

14. The process of claim 1, wherein said first elevated temperature is from about 10° C. to about 100° C.

15. The process of claim 1, wherein said second elevated temperature is higher than the melting temperature of said matrix material.

16. The process of claim 1, wherein said step of granulating is carried out in an intensive mixer without a heating jacket.

17. The process of claim 1, wherein said step of forming the fluidized bed is carried out in a fluidized bed granulator or in a Wuster.

* * * * *